United States Patent
Melsheimer et al.

(10) Patent No.: US 9,314,358 B2
(45) Date of Patent: Apr. 19, 2016

(54) EMERGENCY VASCULAR REPAIR PROSTHESIS DEPLOYMENT SYSTEM

(71) Applicant: Cook Medical Technologies LLC, Bloomington, IN (US)

(72) Inventors: Jeffry S. Melsheimer, Springville, IN (US); Robert M. Eells, Bloomington, IN (US); Grant T. Hoffman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 146 days.

(21) Appl. No.: 14/181,836

(22) Filed: Feb. 17, 2014

(65) Prior Publication Data
US 2014/0200650 A1 Jul. 17, 2014

Related U.S. Application Data

(62) Division of application No. 12/976,121, filed on Dec. 22, 2010, now Pat. No. 8,657,866.

(51) Int. Cl.
*A61F 2/06* (2013.01)
*A61F 2/966* (2013.01)
*A61F 2/97* (2013.01)
*A61F 2/82* (2013.01)

(52) U.S. Cl.
CPC .................. *A61F 2/966* (2013.01); *A61F 2/064* (2013.01); *A61F 2/82* (2013.01); *A61F 2/97* (2013.01)

(58) Field of Classification Search
CPC ........... A61F 2/966; A61F 2/82; A61F 2/064; A61F 2/97; A61F 2002/9511; A61F 2/95
See application file for complete search history.

(56) References Cited

U.S. PATENT DOCUMENTS

| | | | |
|---|---|---|---|
| 2,601,564 A | 6/1952 | Smith |
| 4,306,562 A | 12/1981 | Osborne |
| 4,307,737 A | 12/1981 | Shipman |
| 4,581,025 A | 4/1986 | Timmermans |
| 5,320,602 A | 6/1994 | Karpiel |
| 5,346,498 A | 9/1994 | Greelis et al. |
| 5,380,304 A | 1/1995 | Parker |
| 5,591,226 A | 1/1997 | Trerotola et al. |
| 5,647,857 A | 7/1997 | Anderson et al. |
| 5,707,376 A | 1/1998 | Kavteladze et al. |
| 5,957,929 A | 9/1999 | Brenneman |
| 6,171,234 B1 | 1/2001 | White et al. |
| 6,206,931 B1 | 3/2001 | Cook et al. |
| 6,318,378 B1 | 11/2001 | Kennedy et al. |
| 6,432,127 B1 | 8/2002 | Kim et al. |
| 6,447,540 B1 | 9/2002 | Fontaine et al. |
| 6,562,049 B1 | 5/2003 | Norlander et al. |

(Continued)

*Primary Examiner* — Richard Louis
(74) *Attorney, Agent, or Firm* — Brinks Gilson & Lione

(57) ABSTRACT

A deployment device for repair of a transected body vessel is described herein. Device can have a handle and one or more shafts coupled thereto. A prosthesis being retained by a sheath can be coupled to the delivery device. The sheath can have end portions coupled to one or more shafts. Rotation of a shaft can retract a sheath portion away from either end of the prosthesis for expansion thereof prior to the middle of the prosthesis. Continued rotation of a shaft can completely remove the sheath from the prosthesis, so that the prosthesis is fully expanded and couples the first and second vessel portions of the transected vessel together. Prosthesis may be retained by overlapping a tubular sheath and lacing a threading member therethrough. Prosthesis may be retained by a splittable sheath.

21 Claims, 9 Drawing Sheets

(56) References Cited

U.S. PATENT DOCUMENTS

| | | |
|---|---|---|
| 6,676,666 B2 | 1/2004 | Vrba et al. |
| 6,692,464 B2 | 2/2004 | Graf |
| 6,712,791 B2 | 3/2004 | Lui et al. |
| 6,827,731 B2 | 12/2004 | Armstrong et al. |
| 6,939,337 B2 | 9/2005 | Parker et al. |
| 7,069,935 B2 | 7/2006 | Bousfield et al. |
| 7,244,444 B2 | 7/2007 | Bates |
| 7,294,135 B2 | 11/2007 | Stephens et al. |
| 7,413,573 B2 | 8/2008 | Hartley et al. |
| 7,635,342 B2 | 12/2009 | Ferry et al. |
| 7,691,140 B2 | 4/2010 | Bates et al. |
| 8,114,032 B2 | 2/2012 | Ferry et al. |
| 2004/0010265 A1 | 1/2004 | Karpiel |
| 2004/0204702 A1 | 10/2004 | Ziegler et al. |
| 2005/0080476 A1 | 4/2005 | Gunderson et al. |
| 2007/0010867 A1 | 1/2007 | Carter et al. |
| 2007/0198077 A1* | 8/2007 | Cully et al. ............ 623/1.12 |
| 2007/0219617 A1 | 9/2007 | Saint |
| 2007/0225659 A1 | 9/2007 | Melsheimer |
| 2007/0244540 A1 | 10/2007 | Pryor |
| 2008/0221659 A1* | 9/2008 | Hartley et al. ............ 623/1.13 |
| 2009/0112237 A1 | 4/2009 | Paul, Jr. et al. |
| 2009/0138066 A1 | 5/2009 | Leopold et al. |
| 2009/0259287 A1 | 10/2009 | Valaie |
| 2009/0270969 A1* | 10/2009 | Fargahi et al. ............ 623/1.11 |
| 2009/0319022 A1 | 12/2009 | Hartley et al. |

* cited by examiner

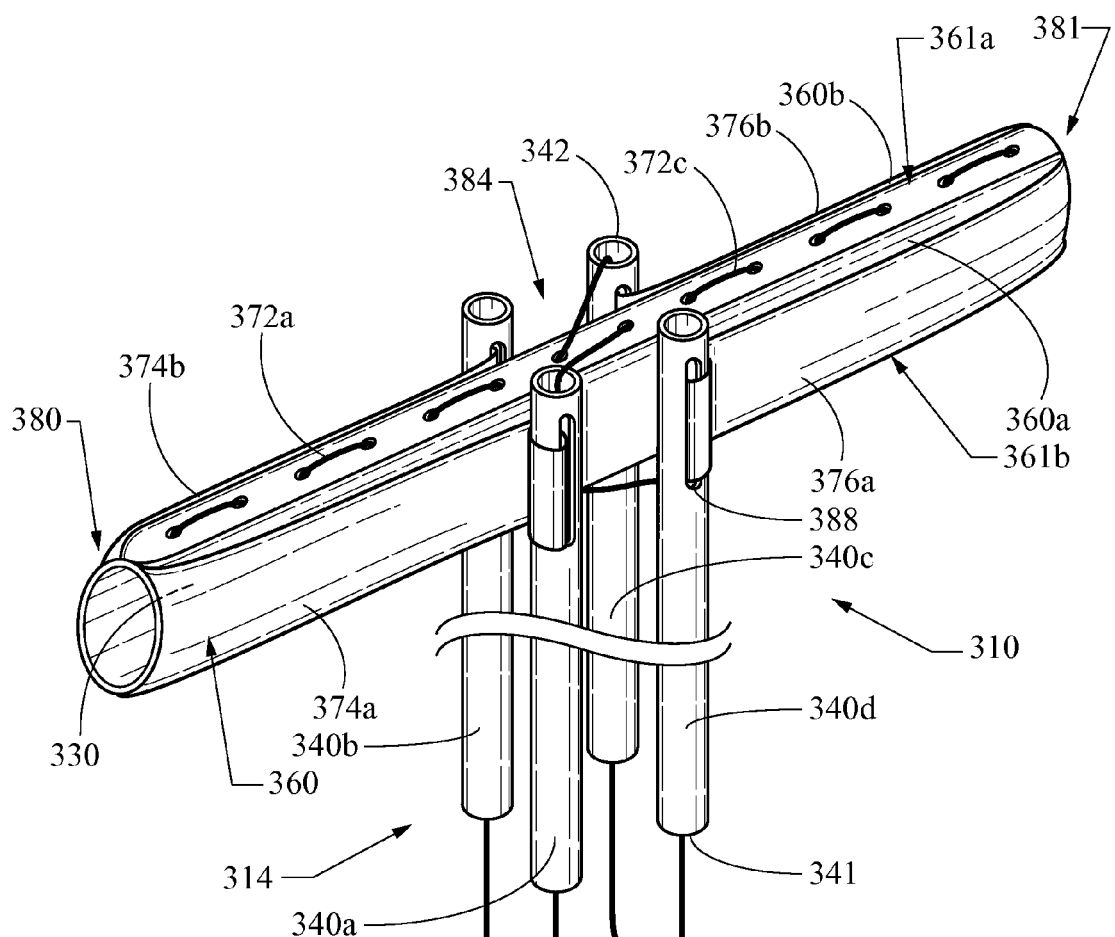
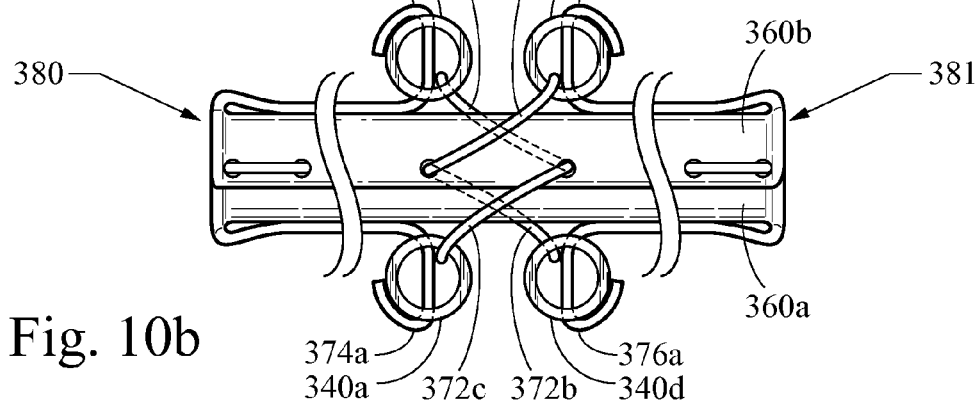
Fig. 10a
Fig. 10b

EMERGENCY VASCULAR REPAIR PROSTHESIS DEPLOYMENT SYSTEM

This application is a divisional of U.S. patent application Ser. No. 12/976,121, filed Dec. 22, 2010, which is incorporated herein by reference in its entirety.

BACKGROUND

The present disclosure relates generally to medical devices for emergency repair of body vessels. More particularly, it relates to deployment systems used for repairing damaged body vessels and gaining hemostasis during emergency medical procedures.

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include the clamping of the vessel with a hemostat, the use of a balloon tamponade, the ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the trauma physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. With respect to ligation, ligation of the damaged blood vessel may result in muscle necrosis, loss of muscle function, or a potential limb loss or death.

Due to the nature of the body vessel injury that may be encountered, the insertion of shunts or ligation of a blood vessel, for example, often requires that such treatments be rapidly performed at great speed, and with a high degree of physician skill. Such treatments may occupy an undue amount of time and attention of the trauma physician at a time when other pressing issues regarding the patient's treatment require immediate attention. In addition, the level of particularized skill required to address a vascular trauma may exceed that possessed by the typical trauma physician. Particularly, traumatic episodes to the vessel may require the skills of a physician specially trained to address the particular vascular trauma, and to stabilize the patient in the best manner possible under the circumstances of the case.

Some open surgical techniques utilize sutures to affix damaged tissue portions surrounding fittings that have been deployed with the vessel, which requires the trauma physician to take time to tie the sutures properly. Although in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in the tissue separating at the point of the sutures. In this event, the connection between the vessel and the fitting may eventually become weakened and subject to failure. If the connection fails, the device may disengage from the vessel. Therefore, efforts continue to develop techniques that reduce the physician time required for such techniques, so that this time can be spent on other potentially life-saving measures, and the blood flow is more quickly restored and damage caused by lack of blood flow is minimized.

Trauma physicians generally find it difficult to manipulate a prosthesis for insertion into a body vessel that has been traumatically injured. For example, one difficulty arises from the trauma physician trying to limit the size of the opening created for gaining access to the injured vessel so that such opening requiring healing is as small as possible. Another difficulty is that the injured vessel can be anywhere in the body, having different surrounding environments of bone structure, muscle tissue, blood vessels, and the like, which makes such obstructions difficult to predict in every situation and leaves the trauma physician working with an even further limited access opening. Another potential consideration is the amount of body vessel removed during a transection. The goal would be to remove a portion of the body vessel as small as possible. Yet, a small portion removed from the vessel leaves such a small space between the two vessel portions, thereby making it difficult to introduce the prosthesis between the two vessel portions.

Thus, what is needed is a deployment device for delivering a prosthesis for use in repair of an injured body vessel, such as an artery or a vein, (and in particular a transected vessel) during emergency surgery. It would be desirable if such deployment device is easy for a trauma physician to use, and can rapidly introduce a prosthesis into two vessel portions of a transected vessel, thereby providing a conduit for blood within the injured body vessel.

SUMMARY

Accordingly, a deployment device is provided herein to address at least some of the shortcomings of the prior art. The deployment device can be used for intraoperative repair of a transected body vessel. A prosthesis can be retained by a removable sheath that is coupled to the delivery device. In one example, the deployment device includes a handle portion and an actuation portion. The handle portion can have a proximal end and a distal end. The actuation portion can include at least one shaft coupled to an actuation member. The shaft can be coupled to the handle portion, and can have a portion coupled to at least one of the extended end portions of the removable sheath. The removable sheath is retractable in a direction toward a center of the prosthesis away from a first outer end and a second outer end of the prosthesis. Both of the first outer end and the second outer end of the prosthesis are capable of being expanded prior to the expansion of the center of the prosthesis.

In another example, a deployment system is provided herein, included a deployment device and a prosthesis assembly. The prosthesis assembly can include a self-expanding prosthesis having a first outer end, a second outer end, and a middle portion therebetween. A removable sheath having a tubular intermediate portion can retain the prosthesis in a radially compressed configuration. The sheath can have a first extended end portion and a second extended end portion each extending away from the intermediate portion. The deployment device can include a handle portion having a proximal end and a distal end adjacent the prosthesis assembly. A first shaft and a second shaft can be coupled to an actuation member and the handle portion. The first shaft can be coupled to the first extended end portion of the sheath, and the second shaft can be coupled to the second extended end portion of the sheath. In response to rotation of each of the first and second shafts, the first and second extended end portions of the sheath are capable of retraction in a direction toward the middle portion of the prosthesis away from the respective first and second outer ends of the prosthesis. Both of the first and second outer ends of the prosthesis are capable of being expanded prior to the expansion of the middle portion of the prosthesis.

In yet another example, a method of intraoperatively repairing a transected body vessel having first and second vessel portions with an end opening is provided. A delivery device including a handle portion and at least one shaft coupled thereto is provided. A prosthesis assembly disposed at an end of the delivery device is also provided, and includes a prosthesis retained by a sheath. A first length of the prosthesis assembly corresponding to a first outer end of the prosthesis can be inserted into an end opening of the first vessel portion. A second length of the prosthesis assembly corresponding to a second outer end of the prosthesis can be inserted into an end opening of the second vessel portion. The at least one shaft can be rotated for removal of a first outer portion of the sheath from the prosthesis in a first direction for expansion of the first outer end of the prosthesis in order to purchase a vessel wall of the first vessel portion. The at least one shaft can be rotated for removal of a second outer portion of the sheath from the prosthesis in a second direction, opposite the first direction, for expansion of the second outer end of the prosthesis in order to purchase a vessel wall of the second vessel portion. To this end, the prosthesis can be fully expanded to couple the first and second vessel portions together.

BRIEF DESCRIPTIONS OF THE DRAWINGS

FIG. 9b is a side view of the stent deployment device of FIG. 9a.

FIG. 9c is a top view of the stent deployment device of FIG. 9a.

FIG. 10a is a perspective partial view of another stent deployment device.

FIG. 10b is a top view of the stent deployment device of FIG. 10a.

DETAILED DESCRIPTION OF THE DRAWINGS AND THE PRESENTLY PREFERRED EMBODIMENTS

Figure 1:
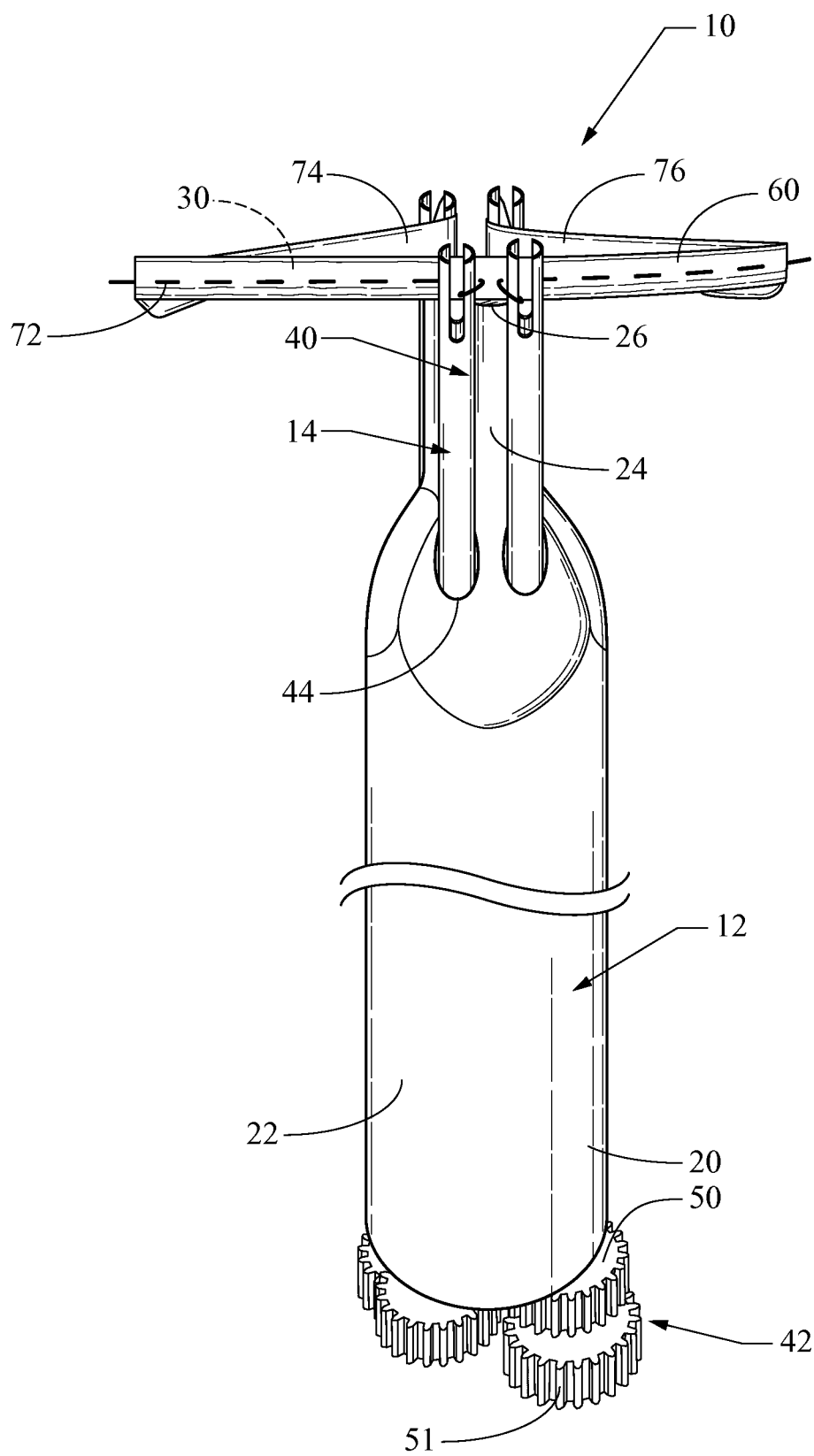
FIG. 1 is a perspective view of a deployment device preloaded with a prosthesis.

For the purposes of promoting an understanding of the principles of the present disclosure, reference will now be made to the embodiments illustrated in the drawings, and specific language will be used to describe the same. The deployment device described herein can be useful for repair of a body vessel, such as a blood vessel, during an emergency open surgical procedure or intraoperative repair. This device can be particularly useful for introducing a prosthesis for repair of a lacerated artery or vein during emergency surgery, and particularly, to obtain hemostasis while maintaining blood perfusion. Other applications for the deployment device will become readily apparent to one skilled in the art from the detailed description.

FIG. 1 depicts one embodiment of a deployment device 10 having a handle portion 12 and an actuation portion 14. Handle portion 12 can include an elongate body 20 having a proximal portion 22 configured to be manipulated and handled by a clinician, and preferably sized to fit within the hands of a clinician. Proximal portion 22 is shown as a cylindrical body, but can be any shape as appreciated by those skilled in the art. A distal portion 24 can extend from proximal portion 22, which can have a smaller cross-sectional area than the proximal portion. Distal portion 24 has an axial end 26 that is shown adjacent to a prosthesis 30. Axial end 26 may be configured to receive and at least partially retain prosthesis 30 in place during delivery of device 10 and deployment of the prosthesis. For example, axial end 26 may be U-shaped or saddle shaped, the center of which receives prosthesis 30. Axial end 26 may be further configured to selectively engage and disengage from prosthesis 30. For example, the axial end may have a clamping member that is operable to open and close from engagement with the prosthesis. Handle portion 12 can be machined or molded from a biocompatible material as can be appreciated by those skilled in the art.

Actuation portion 14 can include one or more shafts 40 coupled to an actuation member 42 that is configured to apply rotation and torque to the shaft. Shaft 40 can be inserted through a corresponding axial chamber 44 formed in handle portion 12. Chamber 44 can include additional features, such as bearings and/or lubrication, to facilitate rotation of the shaft. Shaft 40 can also extend proximally and distally beyond proximal portion 22 of handle portion 12. As shown, shaft 40 may extend alongside distal portion 24 of the handle portion. Shaft 40 can be elongate tubular body or a solid body formed from any biocompatible material, such as stainless steel (e.g., 316L SS), titanium, tantalum, nitinol or other shape memory materials, or a high-strength polymer.

Figure 9A:
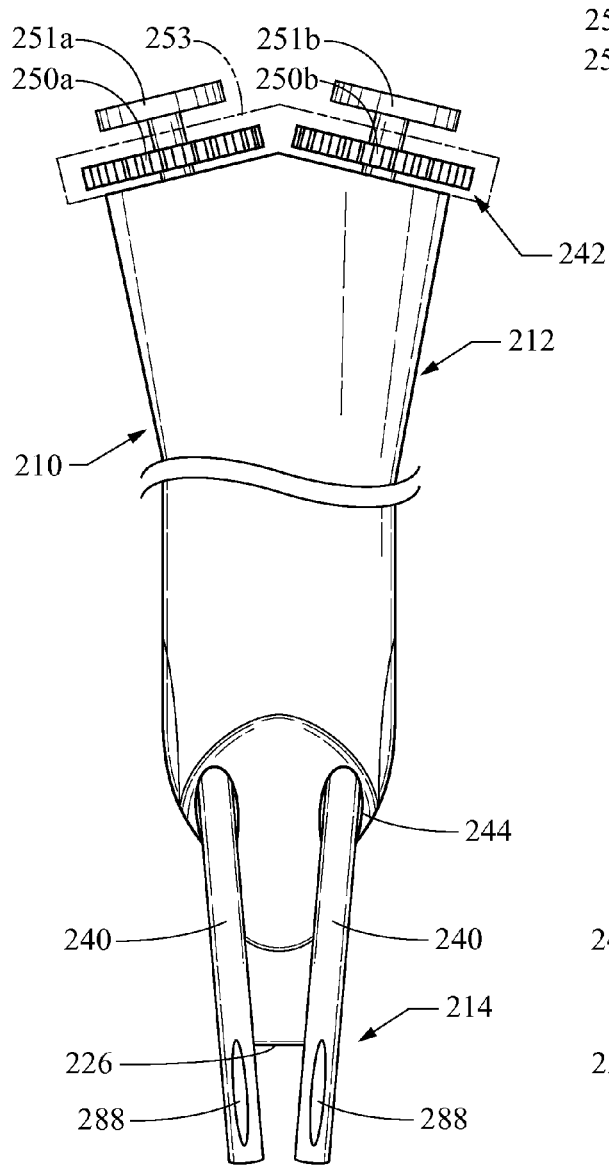
FIG. 9a is a front view of another stent deployment device.

Actuation member 42 is coupled to the proximal end of shaft 40. Actuation member 42 is configured to rotate the shaft 40 in a desired direction, and preferably in an individual manner when more than one shaft is present. In one example, actuation member 42 comprises one or more gears 50 and/or control knobs 51 coupled to the shafts. Gears 50 can be operably coupled to one another in a manner to achieve the desired rotation and torque for a single shaft or each of the shafts. It is further contemplated that each shaft 40 can be rotated at a different speed, direction, and torque depending on the gear configuration as appreciated by those skilled in the art. Control knob 51 is operably coupled to the gears 50, and is configured to be directly handled by the clinician to actuate gear movement. In one example, there can be one control knob for sheath removal from one end, and a second control knob for sheath removal from the opposite end, as shown in FIG. 9c. It is further contemplated that there can be a single control knob for sheath removal from both ends. The control knob can be externally accessible by the clinician, while the gears can be housed within an enclosure. Actuation member 42 can further comprise a driver coupled to the shafts, such as an electric motor coupled to a power source and/or controls for electronically controlling the speed, direction, and torque of shafts 40.

Figure 2A:
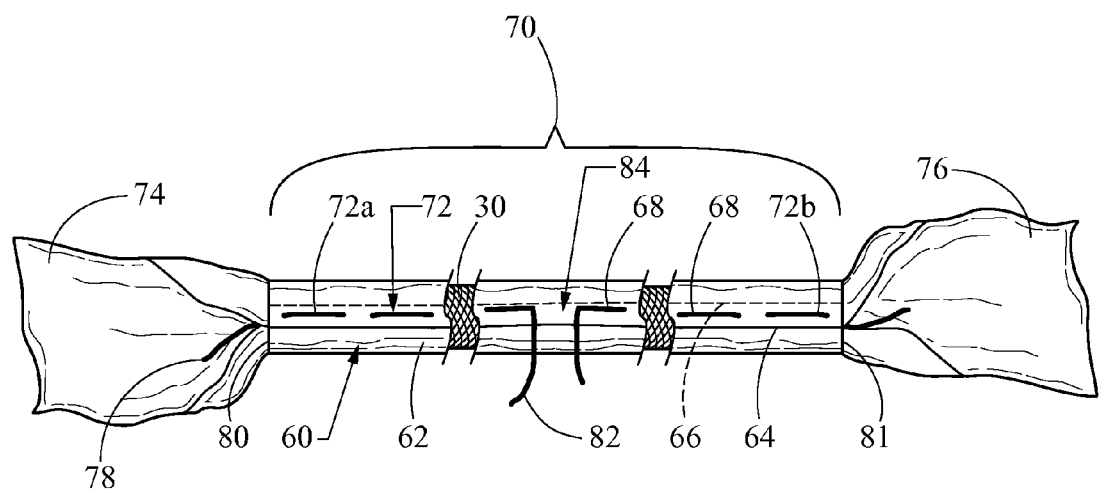
FIG. 2a is a perspective view of a prosthesis being retained in a radially compressed configuration by an overlapping sheath.

Prosthesis 30 can be retained in a compressed configuration by a sheath 60 to form a prosthesis assembly. To allow expansion of prosthesis 30, deployment device 10 can be configured in such a manner to remove sheath 60 from prosthesis 30. With additional reference to FIG. 2a, sheath 60 may be formed from a sheet 62 of material that is rolled in tubular form having a first longitudinal edge 64 overlapping a portion of a second longitudinal edge 66. A series of openings 68 can be formed through at least an intermediate portion 70 of sheath 60. Openings 68 are sized to receive a threading member 72 that is laced through each opening 68 to couple the first and second longitudinal edges 64, 66 together. Alternatively, the overlapping regions of the sheath can be coupled by an adhesive, welding, soldering, or other joining mechanisms and removed in a similar manner as a splittable sheath as described below. The intermediate portion 70 can be sized to at least span the axial length of the prosthesis 30. End portions 74, 76 of sheath 60 adjacent the intermediate portion 70 may remain in a non-overlapping configuration. A system having the threading member laced through the overlapping portions can provide sufficient strength to retain the prosthesis in the compressed configuration, while allowing a minimal torque to peel away the sheath from the prosthesis. In other words, once the threading member is removed from a length of the overlapping portions, only a small torque is required to be provided to the gear/control knob assembly to remove the end portion of the sheath from the prosthesis.

Sheath 60 can be made of any material that is biocompatible, such as polyethylene, polypropylene, or PTFE, and suitable to retain a radially compressed prosthesis. For instance, the sheath material can have excellent tensile strength, minimal elasticity or elongation percentage, and/or high notch resistance. One exemplary material with these characteristics is KAPTON®, available from DuPont, which is a polyimide film, although other material having similar characteristics may be used as appreciated by one skilled in the art. In one example, the sheath material is 0.0015-inch KAPTON®.

A concise description of prosthesis 30 will now be provided. The prosthesis can include a generally tubular graft body and/or one or more anchoring members and/or supporting members together defining a fluid passageway. The prosthesis is movable between a radially compressed, delivery configuration and a radially expanded, deployed configuration. The prosthesis can be balloon expandable; however, it is preferred that the prosthesis is self-expandable. The anchoring members and/or supporting members can be attached to the graft body by sutures sewn therein, wire, staples, clips, bonding agents, or other methods that may be used to achieve a secure attachment to the graft body. The prosthesis has a size and shape suitable for at least partial placement within a body vessel, such as an artery or vein, and most particularly, for placement at the site of a vascular trauma. The prosthesis may be easily manipulated during delivery to a transected artery or vein during emergency surgery, and particularly, to obtain hemostasis while maintaining blood perfusion. The anchoring member and/or supporting member can be any stent pattern known to one skilled in the art. Examples of stent patterns is the Z-STENT® and ZILVER® stent, each available from COOK, INC. (Bloomington, Ind.). The anchoring member and/or supporting member can be formed of a biocompatible metal, such as stainless steel (e.g., 316L SS), titanium, tantalum, nitinol or other shape memory materials, or a high-strength polymer. Preferably, anchoring devices can be included on at least the anchoring members to provide vessel fixation, while avoiding adverse conditions associated with disturbing the vasa vasorum and/or pressure induced necrosis of the medium muscular arteries of the type that may result from tying ligatures circumferentially around a connector or a vascular conduit. The anchoring devices can include various shaped member structures, including barbs, fibers, bristles, or outer protruding and penetrable media.

The graft body can be formed from conventional materials well known in the medical arts. The graft body may comprise an expanded polytetrafluoroethylene (ePTFE), polytetrafluoroethylene, silicone, polyurethane, polyamide (nylon), as well as other flexible biocompatible materials. The graft body can also be formed from known fabric graft materials such as woven polyester (e.g. DACRON®), polyetherurethanes such as THORALON® from Thoratec Corporation, Pleasanton, Calif., polyethylene such as an ultra-high molecular weight polyethylene (UHMwPE), commercially available as DYNEEMA®. The graft body may also include a bioremodelable material, such as reconstituted or naturally-derived collagenous materials, extracellular matrix material (ECM), submucosa, renal capsule membrane, dermal collagen, dura mater, pericardium, fascia lata, serosa, peritoneum or basement membrane layers, intestinal submucosa, including small intestinal submucosa (SIS), stomach submucosa, urinary bladder submucosa, and uterine submucosa. One non-limiting example of a suitable remodelable material is the SURGISIS® BIODESIGN™, commercially available from Cook Incorporated, Bloomington, Ind. Another suitable remodelable material is the graft prosthesis material described in U.S. Pat. No. 6,206,931 to Cook et al., incorporated herein by reference.

Portions of the prosthesis can also include a coating of one or more therapeutic agents along a portion of the stent structure and/or the graft body. Therapeutic agents for use as biocompatible coatings are well known in the art. Non-limiting examples of suitable bio-active agents that may be applied to the vascular conduit include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof Those skilled in the art will appreciate that other bioactive agents may be applied for a particular use. The bioactive agent can be incorporated into, or otherwise applied to, portions of the vascular conduit by any suitable method that permits adequate retention of the agent material and the effectiveness thereof for its intended purpose. Although the device has been described in connection with its primary intended use for repair of vascular trauma, those skilled in the art will appreciate that the device may also be used to repair other traumatic conditions. Non-limiting examples of such conditions include aneurysms, such as abdominal aorta aneurysms, and surgery for tumor removal.

Figure 3:
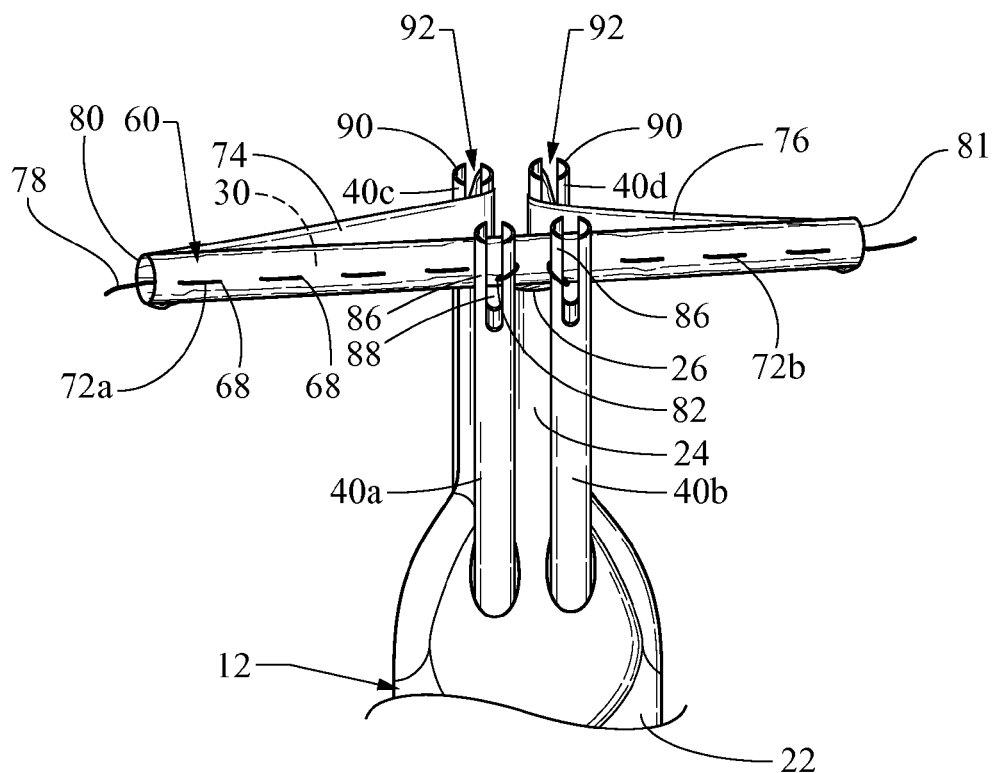
FIG. 3 is a perspective view of a distal end of the deployment device of FIG. 1.

FIG. 3 depicts a four-shaft configuration including a first pair of shafts 40a, 40b and a second pair of shafts 40c, 40d. Prosthesis 30 retained by sheath 60 is disposed along axial end 26, extending laterally between the shafts of the first pair and the shafts of the second pair. With additional reference to FIG. 2a, a first threading member 72a and a second threading member 72b are shown having a length so that a first end 78 of the threading member may extend beyond the respective outer first and second ends 80, 81 of prosthesis 30 (e.g., may extend just beyond the outer ends), being laced through the overlapping region along intermediate portion 70, and having a second end 82 extending out of a center region 84 of the overlapping portion. Second end 82 can be coupled to a distal end 86 of the respective shafts 40a, 40b, or can be positioned within the lumen of the shaft as shown in FIG. 10a. For example, distal end 86 can include an opening 88 extending laterally through the body of the shaft and sized for receiving second end 82 of the respective threading member 72a. Opening 88 may be in the form of an axial slot extending laterally and axially through the body of the shaft. In one example, the opening is closed at the end like the eye of a needle, as shown in FIG. 9a, with the closed portion capable of facilitating removal of the material and threading member from the body after deployment. When the threading member is attached to the shaft, it can be attached by tying, bonding, welding, soldering, clamping with or without a fastener, or the like as appreciated by those skilled in the art. The threading member can be made of any similarly configured structure such as a wire, suture, rope, thread, filament or the like from a biocompatible polymer, fiber, or metal. In one example, the threading member is 0.003-inch by 0.012-inch flat stainless steel wire. Further, the threading member may be round, rectangular, square, polygonal, elliptical, or egg shaped in transverse cross-section. It has been found that a threading member with a rectangular or elliptical transverse cross-section can be advantageous because such threading member has a lower profile in the minor axis and higher flex resistance along the major axis, which can facilitate its removal with the shafts.

End portions 74, 76 are long enough to permit the end portions to be everted or folded back over itself at outer ends 80, 81 of prosthesis 30 in order to be coupled to a distal end 90 of the respective shafts 40c, 40d. For example, distal end 90 can include an opening 92 extending laterally through the body of the shaft and sized for receiving an end of the end portions 74, 76. Opening 92 may be in the form of an axial slot extending laterally and axially through the body of the shaft or may be closed. The end portions of the sheath can be attached to the shaft by tying, bonding, welding, soldering, clamping with or without a fastener, or the like as appreciated by those skilled in the art. The end portions are preferably made of the same sheet of material as the sheath, but it can be appreciated by those skilled in the art that the end portions can be made of a different material with enhanced tensile properties.

Figure 5:
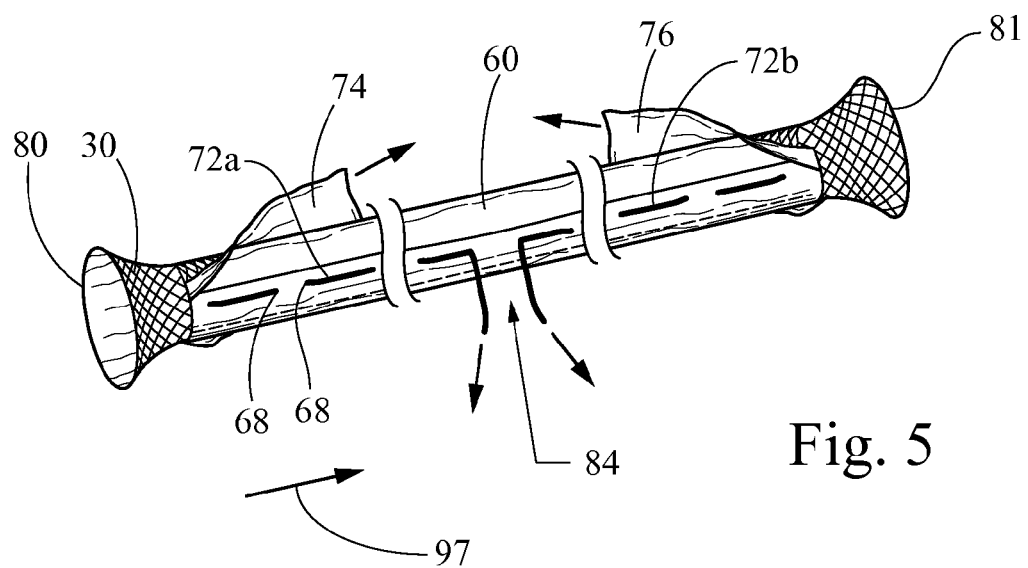
FIG. 5 is a perspective view of the prosthesis of FIG. 2, expanded partially in a radially expanded configuration.
Figure 4:
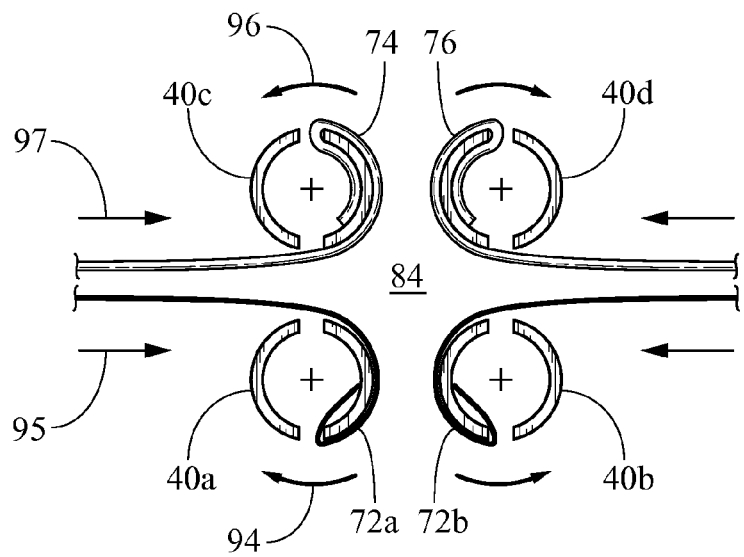
FIG. 4 is a top view of shafts of the deployment device of FIG. 1, depicting operation of the shafts.

FIGS. 4 and 5 better illustrate the operation of deployment device 10 in removing sheath 60 from prosthesis 30 for expansion thereof. One shaft 40a and the adjacent shaft 40c can cooperate to remove a desired portion of sheath 60 from the outer end 80 of prosthesis 30 toward the middle. For example, shaft 40a is rotated in a desired direction, clockwise represented by arrow 94, to move the first wire 72a in a lateral direction, represented by arrow 95, toward center region 84 from openings 68 and wrap first wire 72a around shaft 40a. In a similar fashion, shaft 40c is rotated in the desired direction, counterclockwise represented by arrow 96, to move end portion 74 in a lateral direction, represented by arrow 97, everting or peeling portion of sheath 60 from the outer end 80 of prosthesis 30, and wrapping the end portion 74 and at least partially the remaining sheath portion around shaft 40c. The shafts 40a, 40c can be rotated, preferably synchronously, until sheath 60 has been retracted from outer end 80 of prosthesis 30 in a suitable manner to allow prosthesis 30 to radially expand and purchase the vessel wall. Furthermore, shaft 40b and the adjacent shaft 40d can cooperate to remove sheath 60 from the outer end 81 of prosthesis 30 toward the center region 84 in a similar fashion as shafts 40a, 40c. These shafts 40b, 40d can be rotated, preferably synchronously, until sheath 60 has been retracted from the outer end 81 of prosthesis 30 to radially expand prosthesis 30 and purchase the vessel wall.

As shown in FIG. 5, this arrangement permits expansion of the outer ends 80, 81 of prosthesis 30 to occur before expansion of center region 84. It is contemplated that actuation member 42 can be controlled in a manner to remove sheath 60 from the first outer end 80 and the second outer end 81 sequentially or simultaneously. In other words, shafts 40a, 40c can be rotated first to expand only the first outer end 80 of prosthesis 30, and then shafts 40b, 40d can be rotated to expand the second outer end 81 of prosthesis 30. Alternatively, all of the shafts 40a-d can be rotated at the same time to permit expansion of both of the outer ends 80, 81 of the prosthesis at the same time.

Figure 6A:
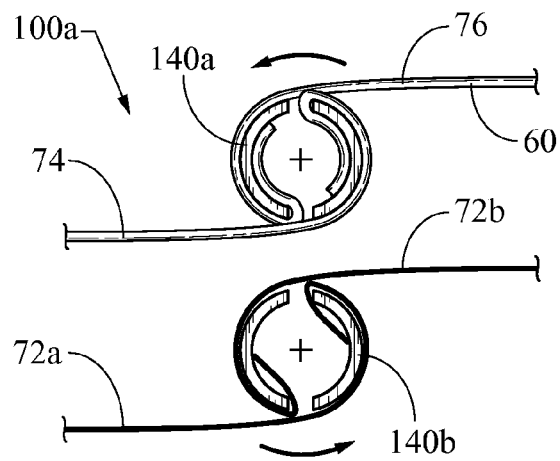
FIGS. 6a-6b are top views of shafts of alternative embodiments of a deployment device.
Figure 6B:
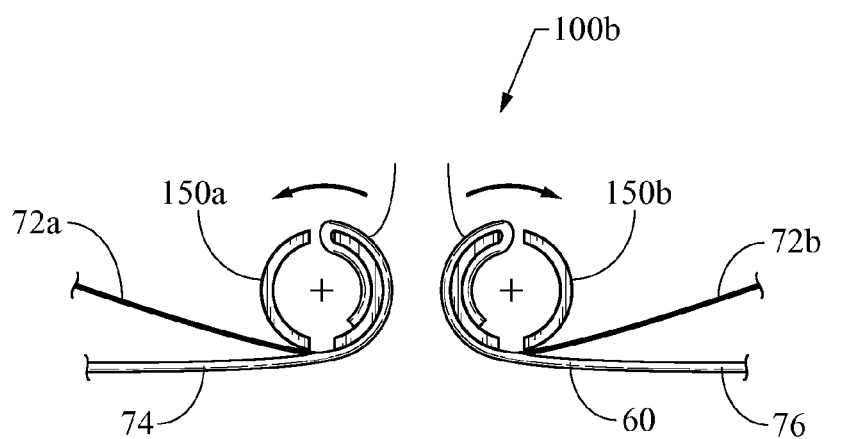

Top ends of other embodiments of the deployment device are shown in FIGS. 6a-6b and FIGS. 7a-7c. For example, FIG. 6a shows a device 100a with a dual-shaft configuration including shafts 140a, 140b, with device 100a having all of the features of device 10 except for the following. End portions 74, 76 of sheath 60 can be attached to a single shaft 140a that is configured to rotate in a direction to remove the sheath from the prosthesis. Threading members 72a, 72b can be attached to a single shaft 140b that is configured to rotate in a direction to remove the threading members from the sheath. FIG. 6b shows a device 100b with a dual-shaft configuration including shafts 150a, 150b, with device 100b having all of the features of device 10 except for the following. End portion 74 of sheath 60 and threading member 72a can be attached to a single shaft 150a that is configured to rotate in a direction to remove the threading member from the sheath and to remove the sheath from the prosthesis. End portion 76 of sheath 60 and threading member 72b can be attached to a single shaft 150b that is configured to rotate in a direction to remove the threading member from the sheath and to remove the sheath from the prosthesis.

Figure 2B:
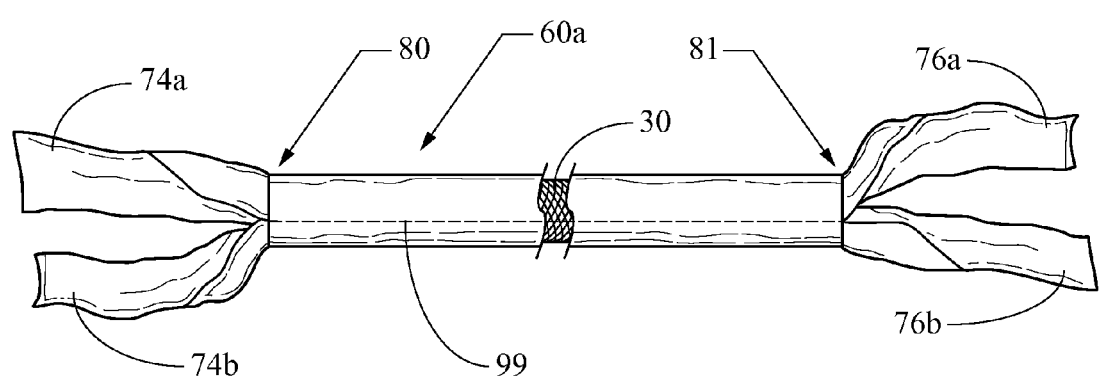
FIG. 2b is a perspective view of a prosthesis being retained in a radially compressed configuration by a splittable sheath.
Figure 7A:
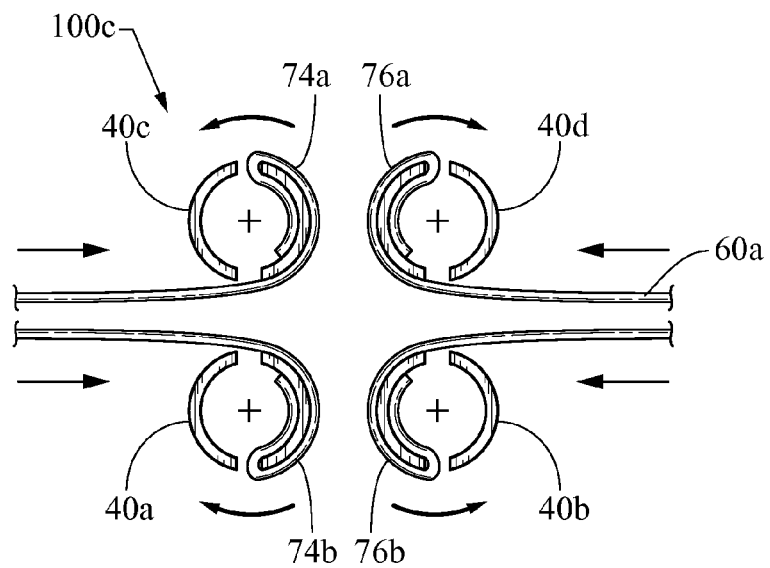
FIGS. 7a-7c are top views of shafts of alternative embodiments of a deployment device, with a splittable sheath retaining the prosthesis.
Figure 7B:
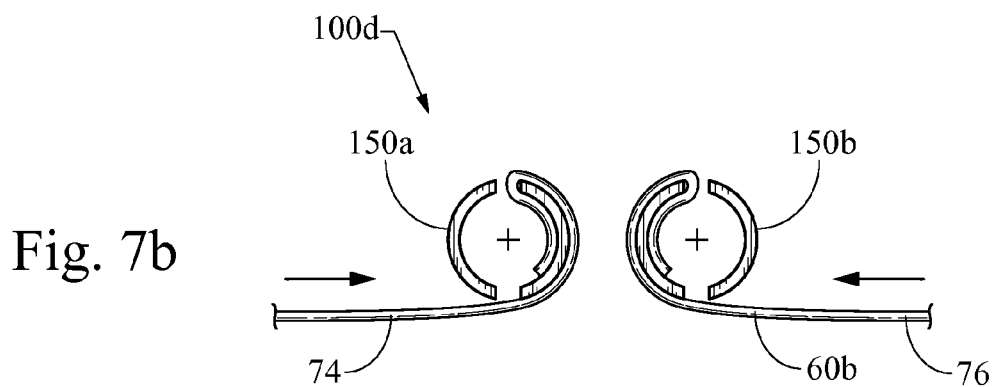
Figure 7C:
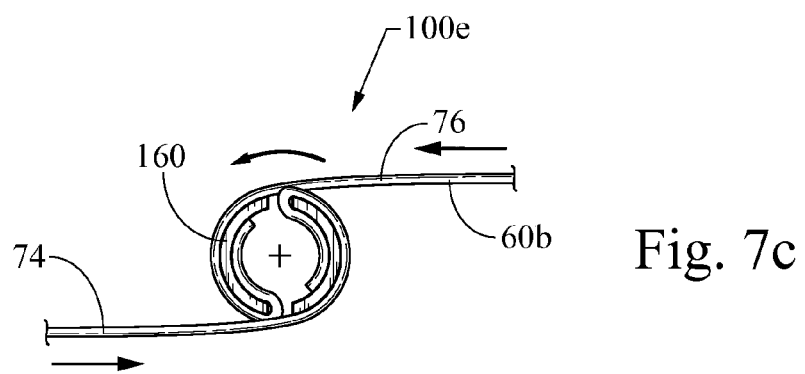

FIG. 7a shows a device 100c with a four-shaft configuration similar to FIG. 4, having all of the features of device 10 except for the following. Instead of the sheath having an overlapping region laced with a threading member, the sheath is a splittable sheath 60a, as shown in FIG. 2b. Sheath 60a can be configured to split to have two end portions 74a, 74b at one end and two end portions 76a, 76b at the other end. As shown, end portions 74a, 74b and 76a, 76b can be coupled to the respective shafts 40a-d. Rotation of shafts can cause sheath 60a to split and to be retracted from the outer ends 80, 81 of prosthesis 30 in a suitable manner to allow prosthesis 30 to radially expand and purchase the vessel wall. FIG. 7b shows a device 100d with a dual-shaft configuration, having all of the features of device 10 except for the following. Instead of the sheath having an overlapping region laced with a threading member, the sheath is a splittable sheath 60b. Here, sheath 60b has one end portion 74 and another end portion 76. As shown, end portions 74, 76 can be coupled to the respective shafts 150a-b. Rotation of shafts 150a, 150b can cause a portion of sheath 60b to further split and to be retracted from the outer ends 80, 81 of prosthesis 30 in a suitable manner to allow prosthesis 30 to radially expand and purchase the vessel wall. In yet another embodiment, FIG. 7c shows a device 100e with a single shaft configuration, having all of the features of device 10 except for the following. Instead of the sheath having an overlapping region laced with a threading member, the sheath is a splittable sheath 60b. Here, sheath 60b has one end portion 74 on one end and one end portion 76 at the other end. As shown, both of end portions 74, 76 can be coupled to the single shaft 160. Rotation of shaft 160 can cause a portions of sheath 60b to further split and to be retracted from the outer ends 80, 81 of prosthesis 30 in a suitable manner to allow prosthesis 30 to radially expand and purchase the vessel wall. Other embodiments of shaft configurations, as well as sheath and/or threading member arrangements, are contemplated with modifications that are consisted with the structure and operation of the deployment device design.

Sheaths 60a, 60b can be splittable by use of any well-known means or material that permits the sheath to be separated, preferably longitudinally, along a relatively predictable path. The sheath is usually, but not necessarily separated into two or more portions, thereby opening a fissure along the length that permits its removal from around the prosthesis situated therein. In FIG. 2b, a predetermined split line 99 (shown by dashed line) may be formed in the sheath through which the tear or split progresses due to properties of, and/or features incorporated into the sheath material. Preferably, the means for splitting the sheath can withstand being subjected to a curve to the degree required by the particular application without kinking or premature separation. In one example, the sheath can comprise a splittable polymer such as molecularly oriented, non-isotropic PTFE that is used to make the PEEL-AWAY® Introducer Sheath (Cook Incorporated, Bloomington, Ind.), which is described in, e.g., U.S. Pat. No. 4,306,562 to Osborne and U.S. Pat. No. 4,581,025 to Timmermans, each of which is incorporated herein by reference in its entirety. In another example, split line 99 can be enhanced by adding at least one preweakened feature, such as a score line, perforations, or reduced wall thickness regions, extending longitudinally along the length of the sheath. The longitudinal preweakened feature may be included anywhere from one or more orthogonal predetermined split lines to a helical type arrangement that may comprise only a single predetermined split line. The preweakened feature may have sheath portions that engage each other with a zipper-like or tongue-and-groove-like interface, or any other splittable connection interface along the contacting lateral edges of the sheath portion. Other examples of splittable sheath configurations can be found in U.S. Pat. No. 6,447,540 to Fontaine et al. and U.S. Pat. No. 6,827,731, each of which is incorporated herein by reference in its entirety. The sheath can have more than one split lines.

Operation of the deployment device will now be discussed. Although the discussion will focus primarily on the operation of deployment device 10, it can be appreciated that the other embodiments of the deployments devices described herein can be similarly operated and used.

Figure 8A:
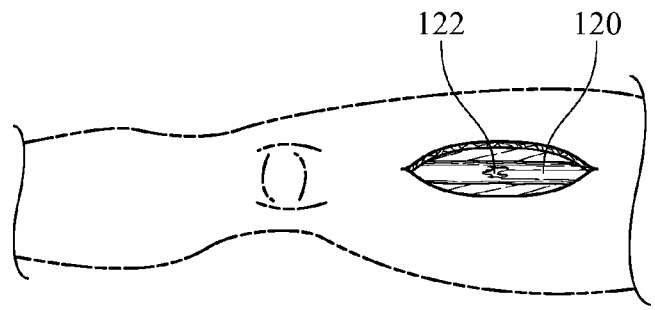
FIGS. 8a-8f illustrate a method of treating a body vessel which has a portion torn away or otherwise severely damaged.
Figure 8B:
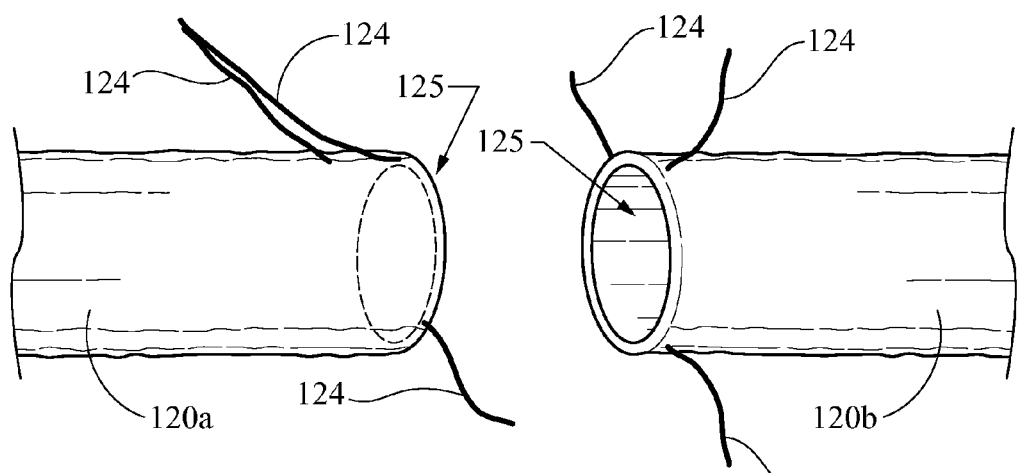

FIGS. 8a-8f illustrate a method of treating a body vessel 120, found for example in the leg of a patient, which has previously been subjected to a traumatic episode, resulting in a portion 122 of body vessel 120 being torn away or otherwise severely damaged. In FIGS. 8a-8b, a body vessel 120, found for example in the leg of a patient, has previously been subjected to a traumatic episode, which results in a portion 122 of body vessel 120 being torn away or otherwise severely damaged. Pre-surgery preparation has been applied to the leg and a trauma pathway may be formed therein in order to gain access to the body vessel and the damaged portion thereof. After clamping body vessel 120 on both ends of the portion 122 to restrict blood flow temporarily, the body vessel 120 can be cut or transected by the clinician into two portions 120a, 120b, as shown in FIG. 8b. The transection may be at the damaged portion 122 of the blood vessel 100 or as far away as necessary from the damaged portion to remove unhealthy portions of the body vessel or unrepairable portions of the body vessel. Sutures 124 can be attached to the end openings 125 of body vessel portions 120a, 120b to keep them fixed in place and opened to facilitate insertion of the prosthesis. Forceps may also be used in a similar manner. Any number of sutures can be used to retain the end openings 125 in the open position, although triangulation sutures can be sufficient, with each suture being about 120 degrees apart from the adjacent suture. A prosthesis is selected to have a radial expanded cross-section and a longitudinal length sufficient to bridge the body vessel portions 120a, 120b and radially fit within the body vessel portions.

Figure 8C:
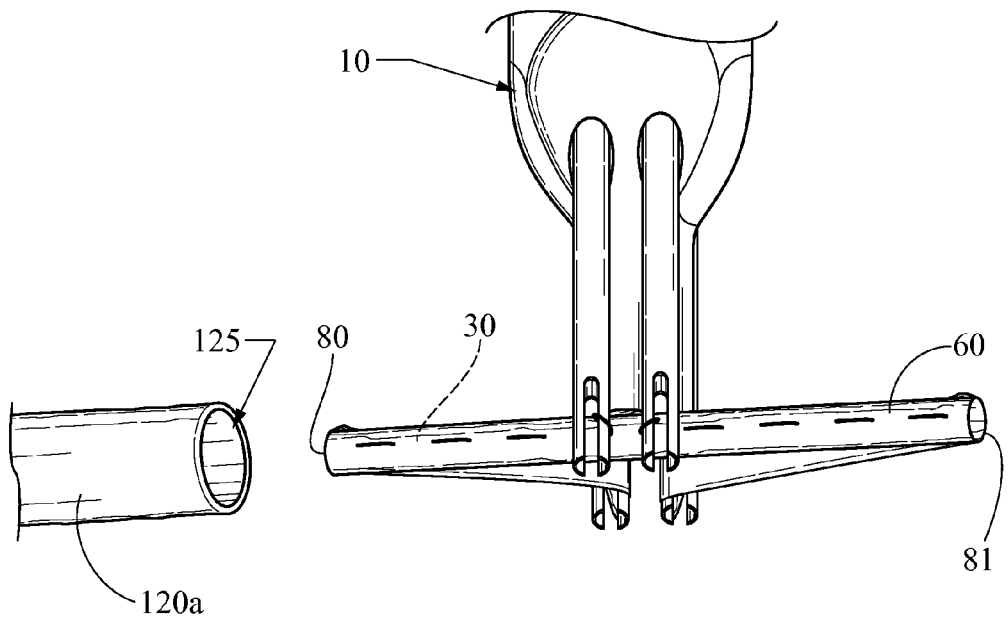

According to FIG. 8c, prosthesis 30, which is preloaded on deployment device 10, is shown being situated and oriented adjacent the body vessel portion 120a through the trauma pathway. Prosthesis 30 is in a delivery configuration, being retained in a radially compressed position by sheath 60. First outer end 80 of prosthesis 30 can be inserted into vessel portion 120a by a sufficient distance for the purposes of anchoring. It is preferred that the vessel portion initially selected be the non-blood supplying vessel end. Vessel portion 120a may be manually pulled over the first outer end 80 of prosthesis 30. After insertion of a portion of prosthesis 30 into end opening 125 of first portion 120a of transected body vessel 120, the actuation member can be operated to rotate the desired shafts for removal of the sheath from first outer end 80 of prosthesis 30, as described herein. This can permit expansion and purchase of a portion of prosthesis 30 along the wall of the vessel portion 120a. Continuation of shaft rotation may occur until that portion of the sheath, as well as the threading member, has been fully retracted from the corresponding portion of the prosthesis and/or completely wrapped around the desired shaft.

Figure 8D:
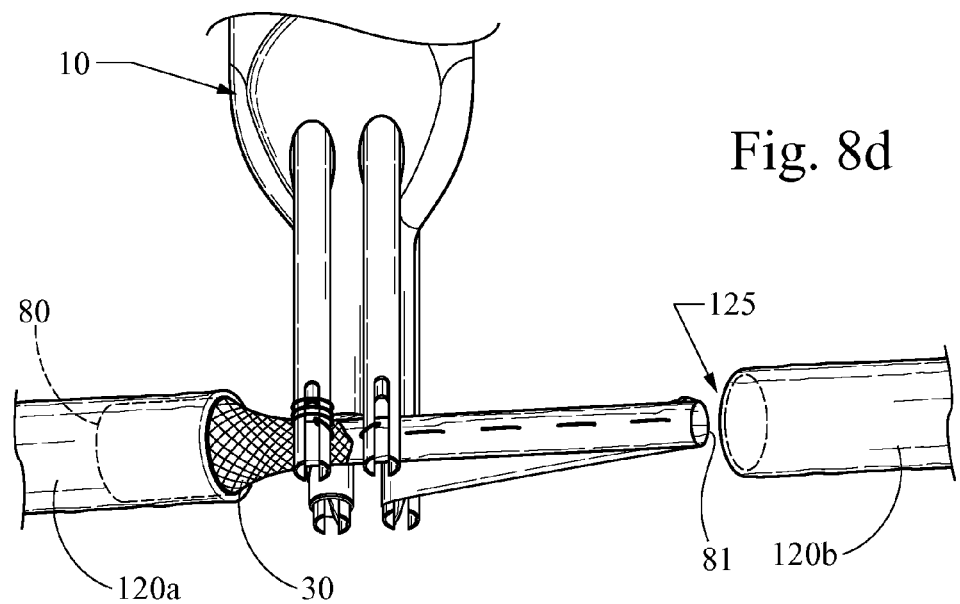

According to FIG. 8d, vessel portion 120a can now be sealably engaged to first outer end 80 of prosthesis 30. Deployment device 10 and prosthesis 30 can then be manipulated in order to introduce second outer end 81 of prosthesis 30 into vessel portion 120b by a sufficient distance for the purposes of anchoring. After insertion of a portion of prosthesis 30 into the end opening 125 of portion 120b of transected body vessel 120, the actuation member can be operated to rotate the desired shafts for removal of the sheath from the second outer end 81 of the prosthesis, as described herein. Thus, the prosthesis is permitted to expand and purchase along the vessel portion 120b. Continuation of shaft rotation may occur until the respective portion of sheath 60, as well as the threading member, has been fully retracted from the corresponding portion of prosthesis 30 and completely wrapped around the desired shaft.

Figure 8E:
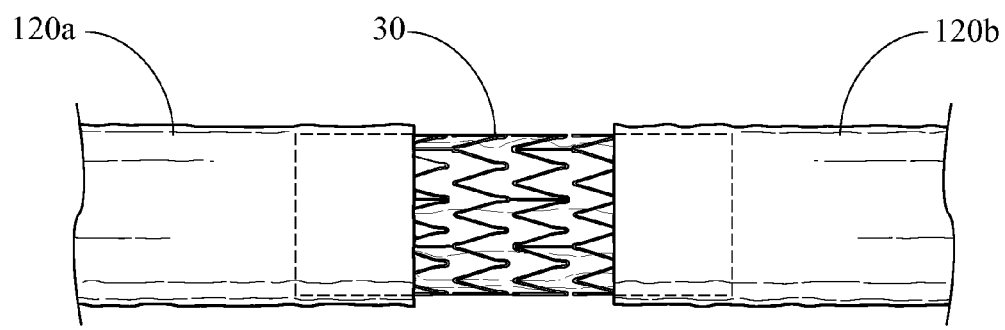

In FIG. 8e, vessel portion 120b can now be sealably engaged to second outer end 81 of prosthesis 30. Accordingly, prosthesis 30 is fully deployed to bridge first and second portions 120a, 120b of the transected body vessel 120 to form a conduit for blood flow. Sutures 124 can then be removed.

Figure 8F:
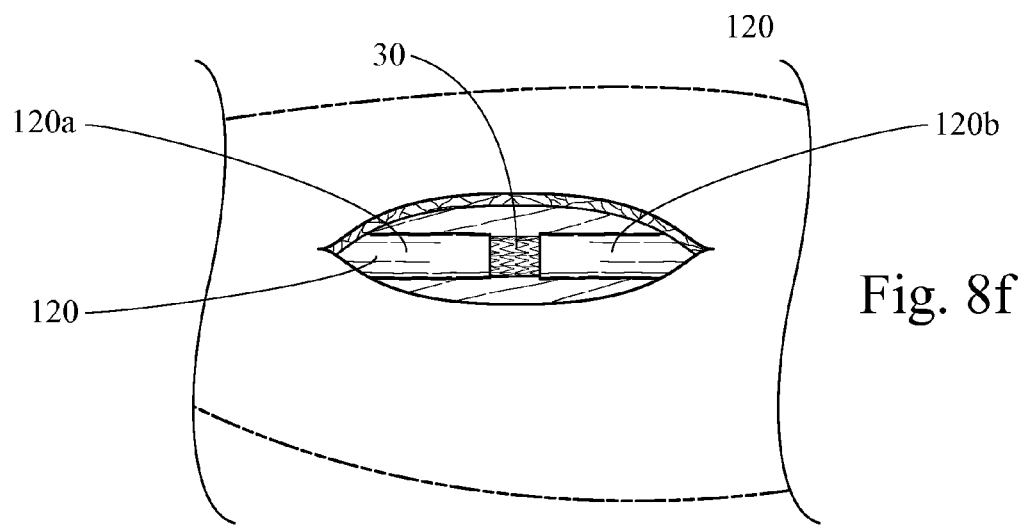

Preferably, portions of the exterior surfaces of the prosthesis sealably engage with the luminal walls of the body vessel to inhibit leakage of blood and to force blood to flow throughout the body vessel during emergency surgery, and particularly to obtain hemostasis while maintaining blood perfusion. FIG. 8f shows the prosthesis 30 deployed and connecting body vessel portions 120A, 120B within the leg of the patient. Prosthesis 30 can be adapted for permanently placement within the patient, thereby obviating a need for subsequent surgical intervention.

Figure 9B:
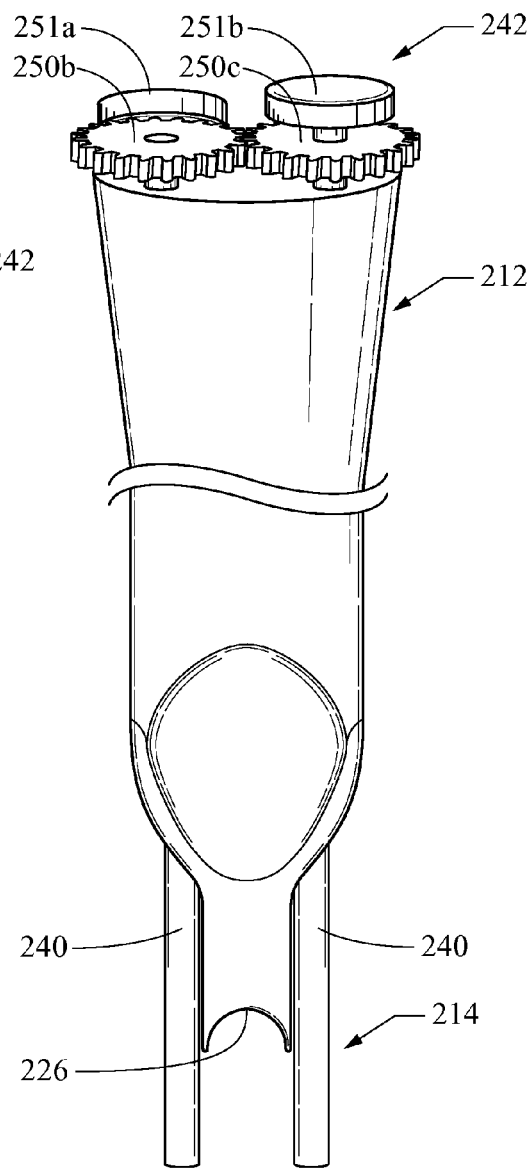
Figure 9C:
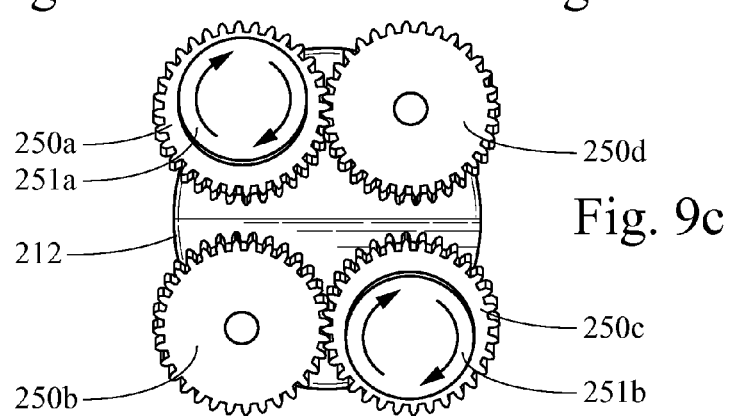

FIGS. 9a-9c depict another embodiment of a deployment device 210 having a handle portion 212 and an actuation portion 214, which have at least some of the same features as device 10. Distal end 226 of handle portion can have a saddle shape for receiving a prosthesis, as shown in FIG. 9b. Actuation portion 214 can include four shafts 240 coupled to actuation member 242 that is configured to apply rotation and torque to the shaft. Shaft 240 can be inserted through a corresponding axial chamber 244 formed in handle portion 212. Actuation member 242 comprises four gears 250a-d and two control knobs 251a-b coupled to shafts 240. A first pair of gears 250b, 250c can be operably coupled to one another in a manner to achieve the desired rotation and torque for a first pair of shafts for removal of the sheath from a first end of the prosthesis. A second pair of gears 250a, 250d can be operably coupled to one another in a manner to achieve the desired rotation and torque for a second pair of shafts for removal of the sheath from the opposite second end of the prosthesis. To this end, actuation of control knob 251a rotates the second pair of shafts, and actuation of control knob 251b rotates the first pair of shafts. In FIG. 9c, the first pair of gears can be spaced from the second pair of gears. Furthermore, the gears may be included within in a gear housing 253, represented by the dashed lines, which can protect the gears and their operation. In FIG. 9a, the first pair of shafts and the second pair of shafts can extend obliquely toward one another, although the shafts can be in parallel. The openings 288 at the distal end of the shafts can be closed in a manner to form an eye of a needle.

FIGS. 10a-10b depict another embodiment of a deployment device 310 having an alternative actuation portion 314 (shown without a handle portion), which have at least some of the same features as devices 10 or 210. FIG. 10a depicts four shafts, a first pair of shafts 340a, 340b and a second pair of shafts 340c, 340d. Prosthesis 330 retained by sheath 360 can be extended laterally between the shafts of the first pair and the shafts of the second pair. Sheath 360 is formed by two sheath portions 360a, 360b which overlap one another along two overlapping regions, a top overlapping region 361a and a bottom overlapping region 361b. First threading member 372a and second threading member 372b can be laced through respective lengths of the top and bottom overlapping regions 361a, 361b along a first end 380. Third threading member 372c and fourth threading member 372d can be laced through respective lengths of the top and bottom overlapping regions 361a, 361b along a second end 381 of the prosthesis.

The ends 382 of the threading members can extend out of a center region 384 of the overlapping portion. Ends 382 are shown threaded through the lumen of the shafts and preferably exiting out a proximal end 341 of the shafts 340a-d. Ends 382 of threading members 372a, 372c can be extended through the distal end opening 342 of the shafts, and the ends 382 of threading members 372b, 372d can be extended through opening 388 of the shafts. To this end, the ends 382 can be withdrawn or pulled in a manner to remove the threading members from the openings of the overlapping portions for expansion of the prosthesis. The ends may be coupled to one another in order to facilitate removal of the threading members with just one pull. The ends may extend beyond the actuation member and be configured like a pull knob. For improved retraction leverage, the ends 382 of threading members 372a, 372b may be extended through the respective distal end opening 342 and the opening 388 of the opposite shafts 340c, 340d, and the ends 382 of threading members 372c, 372d may be extended through the opposite shafts 340a, 340b, as shown in FIG. 10b.

End portions 374a, 376a of the first portion 360a of sheath are long enough to permit the end portions to be everted or folded back over itself in order to be coupled to the respective shafts 340a, 340d. End portions 374b, 376b of the first portion 360b of sheath are long enough to permit the end portions to be everted or folded back over itself in order to be coupled to the respective shafts 340b, 340c.

Rotation of the shafts can remove the end portions from the prosthesis and wind the end portions around the shafts. In one example, to remove sheath 360 from prosthesis 330 for expansion thereof, shafts 340a, 340b can cooperate to remove a desired portion of sheath 360 from the outer end 380 of prosthesis 330 toward the middle. For example, shafts 340a, 340b can be rotated in a desired direction to move the end portions 374a, 374b in a lateral direction toward center region 384 away from first end 380 of prosthesis 330. Further, shafts 340c, 340d can be rotated in a desired direction to move the end portions 376a, 376b away from second end 381 of prosthesis 330 in a lateral direction toward center region 384. This actuation can cause expansion of the first and second ends of the prosthesis, while the end portions are being wrapped around the respective shafts. The closed ended shafts can also capture the wrapped end portions during removal of the delivery system from the body. It can be appreciated by those skilled in the art the sheath portions can be positioned within the shafts, with the threading member coupled to the shafts, in a manner opposite to what is shown in FIG. 10a. It is further contemplated that both components can be configured to pulled through the shafts.

It can be appreciated by those skilled in the art that specific features of each embodiment of the deployment device are interchangeable among the device embodiments, even where no references to the specific features are made.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

We claim:

1. A method of intraoperatively repairing a transected body vessel having first and second vessel portions with first and second end openings, comprising:
    providing a delivery device including a handle portion and at least one shaft coupled thereto;
    providing a prosthesis assembly disposed at an end of the delivery device, the prosthesis assembly comprising a self-expanding prosthesis having first and second outer ends and a middle portion therebetween, and a removable sheath having a tubular intermediate portion retaining the prosthesis in a radially compressed configuration, with first and second extended end portions each extending from the intermediate portion, wherein the first and second extended end portions are coupled to the at least one shaft and wherein the at least one shaft is positioned longitudinally between the first and second outer ends of the prosthesis; and inserting a first length of the prosthesis assembly corresponding to the first outer end of the prosthesis into a first end opening of the first vessel portion;

inserting a second length of the prosthesis assembly corresponding to the second outer end of the prosthesis into a second end opening of the second vessel portion;

rotating the at least one shaft for removal of first extended end portion of the sheath from the prosthesis in a first direction for expansion of the first outer end of the prosthesis in order to purchase a vessel wall of the first vessel portion, and rotating the at least one shaft for removal of second extended end portion of the sheath from the prosthesis in a second direction, opposite the first direction, for expansion of the second outer end of the prosthesis in order to purchase a vessel wall of the second vessel portion, whereby the prosthesis is in a fully expanded configuration and couples the first and second vessel portions together.

2. The method of claim 1, wherein the at least one shaft further comprises first and second shafts coupled to the handle portion, and the rotating step further comprises rotating the first shaft for removal of the first extended end portion of the sheath and for expansion of the first outer end of the prosthesis, and rotating the second shaft for removal of the second extended end portion of the sheath and for expansion of the second outer end of the prosthesis.

3. The method of claim 1, wherein the intermediate portion of the sheath further comprises one or more overlapping regions of longitudinal edges, the overlapping region having a series of openings extending therethrough, and one or more threading members laced through the series of openings, the method further comprising the step of rotating the at least one shaft for removal of the threading member from the series of openings to facilitate expansion of the prosthesis.

4. The method of claim 1, wherein the intermediate portion of the sheath further comprises one or more overlapping regions of longitudinal edges, the overlapping region having a series of openings extending therethrough, and one or more threading members laced through the series of openings, the method further comprising the step of retracting the one or more threading members from the series of openings to facilitate expansion of the prosthesis.

5. The method of claim 1, wherein the intermediate portion of the sheath further comprises one or more longitudinal split regions, the method further comprising the step of splitting the sheath along the one or more longitudinal split regions to facilitate expansion of the prosthesis.

6. The method of claim 1, wherein the at least one shaft extends in a direction transverse to a longitudinal axis of the prosthesis.

7. The method of claim 1, wherein the first and second extended end portions of the sheath are wound around the at least one shaft in response to rotating the at least one shaft.

8. The method of claim 1, wherein the first and second directions are toward a center of the prosthesis, the sheath thereby being retracted toward the center of the prosthesis.

9. The method of claim 1, wherein the at least one shaft further comprises first and second shafts, a first length of the sheath proximate the first outer end of the prosthesis is everted in order to direct the first extended end portion toward the first shaft, and a second length of the sheath proximate the second outer end of the prosthesis is everted in order to direct the second extended end portion toward the second shaft.

10. The method of claim 9, wherein the at least one shaft further comprises a third and fourth shaft, and the sheath further comprises an overlapping region of longitudinal edges, a first threading member laced through a first portion of the overlapping region, a second threading member laced through a second portion of the overlapping region, wherein the third shaft is coupled to the first threading member, and the fourth shaft is coupled to the second threading member, and in response to rotation of the third and fourth shafts by the actuation member, the first threading member is removable and the second threading member is removable from the respective first and second portions of the overlapping region.

11. The method of claim 10, wherein the first and second shafts are capable of winding the respective first and second extended end portions of the sheath there around, and the third and fourth shafts are capable of winding the respective first and second threading members there around.

12. The method of claim 10, wherein one of the first and second shafts and one of the third and fourth shafts form a first pair of shafts, the first pair of shafts configured to synchronously retract the first extended end portion and the first threading member toward the center of the prosthesis away from the first outer end of the prosthesis.

13. The method of claim 12, wherein the other of the first and second shafts and the other of the third and fourth shafts form a second pair of shafts, the second pair of shafts configured to synchronously retract the second extended end portion and the second threading member toward the center of the prosthesis away from the second outer end of the prosthesis.

14. The method of claim 13, wherein the first pair of shafts and the second pair of shafts are rotated in sequence.

15. The method of claim 13, wherein the first pair of shafts and the second pair of shafts are rotated simultaneously.

16. The method of claim 1, wherein the sheath further comprises at least first and second segments, the at least one shaft further comprises first, second, third and fourth shafts, and the sheath further comprises third and fourth extended end portions, the first shaft coupled to the first extended end portion and the first segment of the sheath, the second shaft coupled to the second extended end portion and the first segment of the sheath, the third shaft coupled to the third extended end portion and the second segment of the sheath, and the fourth shaft coupled to the fourth extended end portion and the second segment of the sheath.

17. The method of claim 16, wherein the first and second segments of the sheath form first and second overlapping regions of longitudinal edges, and further comprising a first threading member laced through a first length of the first overlapping region, a second threading member laced through a first length of the second overlapping region, a third threading member laced through a second length of the first overlapping region, a fourth threading member laced through a second length of the second overlapping region, wherein each of the threading members is inserted through the respective shafts, and in response to a retraction force on each of the threading members, each of the threading members is removable from the respective first and second overlapping regions.

18. The method of claim 1, wherein the at least one shaft extends in a direction transverse to a longitudinal axis of the prosthesis, the first and second extended end portions of the sheath are wound around the at least one shaft in response to rotating the at least one shaft, and the first and second directions are toward a center of the prosthesis, the sheath thereby being retracted toward the center of the prosthesis.

19. The method of claim 18, wherein the at least one shaft further comprises first and second shafts coupled to the handle portion, and the rotating step further comprises rotating the first shaft for removal of the first extended end portion of the sheath and for expansion of the first outer end of the prosthesis, and rotating the second shaft for removal of the second extended end portion of the sheath and for expansion of the second outer end of the prosthesis, and the intermediate portion of the sheath further comprises one or more overlapping regions of longitudinal edges, the overlapping region having a series of openings extending therethrough, and one or more threading members laced through the series of openings, the method further comprising the step of rotating the at least one shaft for removal of the threading member from the series of openings to facilitate expansion of the prosthesis.

20. A method of intraoperatively repairing a transected body vessel having first and second vessel portions with first and second end openings, comprising:
providing a delivery device including a handle portion and at least one shaft coupled thereto;
providing a prosthesis assembly disposed at an end of the delivery device, the prosthesis assembly comprising a self-expanding prosthesis having first and second outer ends and a middle portion therebetween, and a removable sheath having a tubular intermediate portion retaining the prosthesis in a radially compressed configuration, with first and second extended end portions each extending from the intermediate portion, wherein the first and second extended end portions are coupled to the at least one shaft; and
inserting a first length of the prosthesis assembly corresponding to the first outer end of the prosthesis into a first end opening of the first vessel portion;
inserting a second length of the prosthesis assembly corresponding to the second outer end of the prosthesis into a second end opening of the second vessel portion;
rotating the at least one shaft for removal of first extended end portion of the sheath from the prosthesis in a first direction for expansion of the first outer end of the prosthesis in order to purchase a vessel wall of the first vessel portion, and rotating the at least one shaft for removal of second extended end portion of the sheath from the prosthesis in a second direction, opposite the first direction, for expansion of the second outer end of the prosthesis in order to purchase a vessel wall of the second vessel portion, whereby the prosthesis is in a fully expanded configuration and couples the first and second vessel portions together,
wherein the intermediate portion of the sheath further comprises one or more overlapping regions of longitudinal edges, the overlapping region having a series of openings extending therethrough, and one or more threading members laced through the series of openings, the method further comprising the step of rotating the at least one shaft for removal of the threading member from the series of openings to facilitate expansion of the prosthesis.

21. A method of intraoperatively repairing a transected body vessel having first and second vessel portions with first and second end openings, comprising:
providing a delivery device including a handle portion and at least one shaft coupled thereto;
providing a prosthesis assembly disposed at an end of the delivery device, the prosthesis assembly comprising a self-expanding prosthesis having first and second outer ends and a middle portion therebetween, and a removable sheath having a tubular intermediate portion retaining the prosthesis in a radially compressed configuration, with first and second extended end portions each extending from the intermediate portion, wherein the first and second extended end portions are coupled to the at least one shaft; and
inserting a first length of the prosthesis assembly corresponding to the first outer end of the prosthesis into a first end opening of the first vessel portion;
inserting a second length of the prosthesis assembly corresponding to the second outer end of the prosthesis into a second end opening of the second vessel portion;
rotating the at least one shaft for removal of first extended end portion of the sheath from the prosthesis in a first direction for expansion of the first outer end of the prosthesis in order to purchase a vessel wall of the first vessel portion, and rotating the at least one shaft for removal of second extended end portion of the sheath from the prosthesis in a second direction, opposite the first direction, for expansion of the second outer end of the prosthesis in order to purchase a vessel wall of the second vessel portion, whereby the prosthesis is in a fully expanded configuration and couples the first and second vessel portions together,
wherein the at least one shaft further comprises first and second shafts, a first length of the sheath proximate the first outer end of the prosthesis is everted in order to direct the first extended end portion toward the first shaft, and a second length of the sheath proximate the second outer end of the prosthesis is everted in order to direct the second extended end portion toward the second shaft,
wherein the at least one shaft further comprises a third and fourth shaft, and the sheath further comprises an overlapping region of longitudinal edges, a first threading member laced through a first portion of the overlapping region, a second threading member laced through a second portion of the overlapping region, wherein the third shaft is coupled to the first threading member, and the fourth shaft is coupled to the second threading member, and in response to rotation of the third and fourth shafts by the actuation member, the first threading member is removable and the second threading member is removable from the respective first and second portions of the overlapping region.

* * * * *